United States Patent [19]

Fey et al.

[11] Patent Number: 5,414,003
[45] Date of Patent: May 9, 1995

[54] PYRIDINYLMETHYL-SUBSTITUTED PYRIDINES AND PYRIDONES

[75] Inventors: Peter Fey, Wuppertal; Jürgen Dressel, Radevormwald; Rudolf Hanko, Essen; Walter Hübsch, Wuppertal; Thomas Krämer, Wuppertal; Ulrich Müller, Wuppertal; Matthias Müller-Gliemann, Solingen; Martin Beuck, Erkrath; Hilmar Bischoff, Wuppertal; Stefan Wohlfeil, Hilden; Dirk Denzer; Stanislav Kazda, both of Wuppertal; Johannes-Peter Stasch, Solingen; Andreas Knorr, Erkrath; Siegfried Zaiss, Wuppertal, all of Germany

[73] Assignee: Bayer Aktiengesellschaft, Leverkusen, Germany

[21] Appl. No.: 235,770

[22] Filed: Apr. 29, 1994

[30] Foreign Application Priority Data

May 6, 1993 [DE] Germany .................. 43 14 964.2

[51] Int. Cl.⁶ ............... C07D 401/14; A61K 31/44; A61K 31/50; A61K 31/53
[52] U.S. Cl. .................. 514/333; 514/332; 514/335; 546/255; 546/256; 546/261; 546/262; 546/264; 546/266
[58] Field of Search ........... 546/256, 261, 255, 262, 546/264, 266; 514/333, 335, 332

[56] References Cited

U.S. PATENT DOCUMENTS

| | | | |
|---|---|---|---|
| 5,128,327 | 7/1992 | Chakravarty et al. | 514/81 |
| 5,149,699 | 9/1992 | Ellingboe et al. | 514/258 |
| 5,155,117 | 10/1992 | Reitz | 514/340 |
| 5,196,537 | 3/1993 | Reitz | 546/276 |

FOREIGN PATENT DOCUMENTS

| | | | |
|---|---|---|---|
| 0487745 | 6/1992 | European Pat. Off. | 546/256 |
| 0499416 | 8/1992 | European Pat. Off. | 546/256 |
| 0508445 | 10/1992 | European Pat. Off. | 546/256 |
| 0510813 | 10/1992 | European Pat. Off. | 546/256 |
| 2696745 | 4/1994 | France | 546/261 |

OTHER PUBLICATIONS

E. L. Eliel, Stereochemistry of Carbon Compounds, McGraw Hill, 1962, 6 pgs.
The Journal of Cell Biology, vol. 5, 1971, pp. 172–186; "The Smooth Muscle Cell . . . ", R. Ross.

Primary Examiner—C. Warren Ivy
Assistant Examiner—Zinna N. Davis
Attorney, Agent, or Firm—Sprung Horn Kramer & Woods

[57] ABSTRACT

Pyridinylmethyl-substituted pyridines and pyridones are prepared by reacting pyridine- or pyridone-substituted halogenopyridines with tetrazolylphenylboronic acids. The substances according to the invention can be used as active compounds in medicaments, in particular for the treatment of arterial hypertension and atherosclerosis.

5 Claims, No Drawings

PYRIDINYLMETHYL-SUBSTITUTED PYRIDINES AND PYRIDONES

The invention relates to pyridinylmethyl-substituted pyridines and pyridonen, to processes for their preparation and to their use in medicaments, in particular as hypotensive and anti-atherosclerotic agents.

It is known that renin, a proteolytic enzyme, eliminates the decapeptide angiotensin I from angiotensinogen in vivo, and the angiotensin I is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, of cardiac muscle cells and smooth muscle cells, these growing and proliferating in an increased manner in various disease states (for example hypertension, atherosclerosis and cardiac insufficiency).

In addition to the inhibition of renin activity, a possible starting point for intervention in the reninangiotensin system (RAS) is the inhibition of the activity of the angiotensin-converting enzyme (ACE) and the blockade of angiotensin II receptors.

Arylheteroarylalkyl-substituted triazoles and imidazoles are disclosed in the publications EP 508 445, EP 503 393, EP 504 888 and US 5 128 327 as A II antagonists.

The present invention relates to phenylpyridinylmethyl-substituted 2-oxo-1,2-dihydropyridines and pyridines of the general formula (I)

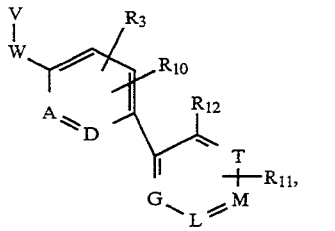

in which
A, D, G, L, M and T are identical or different and represent the CH group or a nitrogen atom, but where at least one of the radicals and in each case at most one of the radicals in each cycle may represent a nitrogen atom,
V represents a radical of the formula

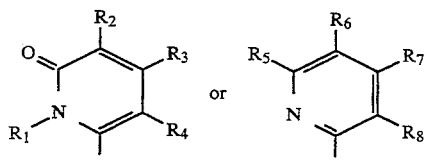

in which
$R^1$ denotes straight-chain or branched alkyl having up to 10 carbon atoms, which is optionally substituted by cycloalkyl having 3 to 6 carbon atoms or hydroxyl or by straight-chain or branched alkoxy or alkylthio in each case having up to 6 carbon atoms, or denotes cycloalkyl having 3 to 6 carbon atoms,
$R^2$, $R^5$ and $R^6$ are identical or different and denote hydrogen, hydroxyl, nitro, cyano, formyl or halogen, or denote straight-chain or branched alkyl, alkenyl, alkinyl, alkoxy or alkylthio in each case having up to 8 carbon atoms, each of which is optionally substituted up to 3 times by identical or different substituents from the group consisting of hydroxyl, cyano, halogen, carboxyl and straight-chain or branched alkoxy, acyl or alkoxycarbonyl in each case having up to 6 carbon atoms, or by cycloalkyl having 3 to 6 carbon atoms, benzyl, phenyl, phenoxy or benzoyl or by a 5- to 7-membered, saturated or unsaturated heterocycle having up to 3 hetero atoms from the group consisting of S, N and O where the cycles for their part can be substituted up to 2 times by identical or different trifluoromethyl, trifluoromethoxy, halogen, nitro, cyano, hydroxyl or hydroxymethyl or by straight-chain or branched alkyl or alkoxy in each case having up to 6 carbon atoms, or denote straight-chain or branched acyl or alkoxycarbonyl in each case having up to 8 carbon atoms, phenoxycarbonyl, benzyloxycarbonyl or carboxyl, or denote tetrazolyl, which is optionally substituted by triphenylmethyl or by straight-chain or branched alkyl having up to 6 carbon atoms, which for its part can be substituted by cyano, halogen, carboxyl, phenoxycarbonyl or hydroxyl or by straight-chain or branched alkoxy or alkoxycarbonyl in each case having up to 6 carbon atoms, or denote a group of the formula

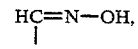

$-NR^{13}R^{14}$, $-CO-NR^{15}R^{16}$, $-CH_2-OR^{17}$ or $-S(O)_a-R^{18}$
in which
$R^{13}$, $R^{14}$, $R^{15}$ and $R^{16}$ are identical or different and denote hydrogen, cycloalkyl having 3 to 8 carbon atoms or straight-chain or branched alkyl having up to 8 carbon atoms, which is optionally substituted by phenyl,
$R^{17}$ denotes straight-chain or branched acyl having up to 6 carbon atoms or benzoyl,
$R^{18}$ denotes straight-chain or branched alkyl having up to 8 carbon atoms,
denotes a number 1 or 2,
$R^3$ and $R^7$ are identical or different and denote hydrogen, hydroxyl, carboxyl, straight-chain or branched alkoxy or alkoxycarbonyl in each case having up to 8 carbon atoms, or denote a group of the formula $-NR^{19}R^{20}$,
in which
$R^{19}$ and $R^{20}$ have the abovementioned meaning of $R^{13}$ and $R^{14}$ and are identical to or different from this, or denote aryl having 6 to 10 carbon atoms, which can optionally be substituted up to 2 times by identical or different substituents from the group consisting of trifluoromethyl, trifluoromethoxy, halogen, nitro, cyano, hydroxyl and hydroxymethyl or by straight-chain or branched alkyl or alkoxy in each case having up to 6 carbon atoms, or denote straight-chain or branched alkyl or alkenyl in each case having up to 8 carbon atoms, each of which is optionally substituted up to 3 times by identical or different substituents from the group consisting of hydroxyl, cyano, halogen, carboxyl and straight-chain or branched alkoxy, acyl or alkoxycarbonyl in each case having up to 6 carbon atoms, or by cycloalkyl having 3 to 6 carbon atoms, benzyl, phenyl, phenoxy, benzoyl or by a 5- to 7-membered, saturated or unsaturated heterocycle having up to 3 hetero atoms from the group consisting of S, N and O where the cycles for their part can be substituted up to 2 times by identical or different trifluoromethyl, trifluoromethoxy, halogen, nitro, cyano, hydroxyl or hydroxymethyl or by straight-chain or branched alkyl or alkoxy in each case having up to 6 carbon atoms, $R^4$ denotes hydrogen, nitro, carboxyl or straight-chain or branched alkoxycarbonyl having up to 8 carbon atoms, or denotes a group of the formula —$NR^{21}R^{22}$, in which $R^{21}$ and $R^{22}$ have the abovementioned meaning of $R^{13}$ and $R^{14}$ and are identical to or different from this, or denotes straight-chain or branched alkyl or alkenyl in each case having up to 8 carbon atoms, each of which is optionally substituted up to 3 times by identical or different substituents from the group consisting of hydroxyl, cyano, halogen, carboxyl and straight-chain or branched alkoxy, acyl or alkoxycarbonyl in each case having up to 6 carbon atoms or by cycloalkyl having 3 to 6 carbon atoms, benzyl, phenyl, phenoxy or benzoyl or by a 5- to 7-membered, saturated or unsaturated heterocycle having up to 3 hetero atoms from the group consisting of S, N and O, where the cycles for their part can be substituted up to 2 times by identical or different trifluoromethyl, trifluoromethoxy, halogen, nitro, cyano, hydroxyl or hydroxymethyl or by straight-chain or branched alkyl or alkoxy in each case having up to 6 carbon atoms, $R^8$ has the abovementioned meaning of $R^1$ and $R^4$ and is identical to or different from this, W represents the

group, or represents a group of the formula

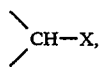

in which

X denotes hydrogen or straight-chain or branched alkyl having up to 8 carbon atoms, $R^9$, $R^{10}$ and $R^{11}$ are identical or different and represent hydrogen, halogen, cyano, nitro, trifluoromethyl, hydroxyl, amido or straight-chain or branched alkyl, alkoxy or alkoxycarbonyl having up to 6 carbon atoms, $R^{12}$ represents a group of the formula —CO—$R^{23}$, —$SO_2R^{24}$, —CO—$NR^{25}R^{26}$, —NH—$SO_2R^{27}$ or —$SO_2NR^{28}R^{29}$, in which $R^{23}$ denotes hydroxyl or straight-chain or branched alkoxy having up to 6 carbon atoms, $R^{24}$ denotes hydroxyl, trifluoromethyl, straight-chain or branched alkoxy or alkyl in each case having up to 6 carbon atoms, phenyl or benzyl, each of which is optionally substituted up to 2 times by identical or different substituents from the group consisting of halogen, trifluoromethyl and straight-chain or branched alkyl having up to 4 carbon atoms, $R^{25}$ and $R^{26}$ are identical or different and have the abovementioned meaning of $R^{13}$ and $R^{14}$, or $R^{25}$ denotes hydrogen and $R^{26}$ denotes the group —$SO_2R^{24}$, in which $R^{24}$ has the abovementioned meaning, $R^{27}$ has the abovementioned meaning of $R^{24}$ and is identical to or different from this, $R^{28}$ and $R^{29}$ have the abovementioned meaning of $R^{13}$ and $R^{14}$ and are identical to or different from this, or $R^{28}$ denotes hydrogen or straight-chain or branched alkyl having up to 4 carbon atoms and $R^{29}$ has the abovementioned meaning of $R^{24}$ and is identical to or different from this, $R^{12}$ represents a radical of the formula

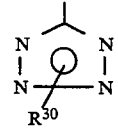

in which $R^{30}$ denotes hydrogen or straight-chain or branched alkyl having up to 8 carbon atoms, which is optionally substituted by straight-chain or branched acyl having up to 6 carbon atoms or denotes the triphenylmethyl group, and their salts.

The phenylpyridinylmethyl-substituted 2-oxo-1,2-dihydropyridines and pyridones according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention, which have a free carboxyl group or a tetrazolyl radical. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can also exist in stereoisomeric forms which either behave as image and mirror image (enantiomers), or which do not behave as image and mirror image (diastereomers). The invention relates either to the enantiomers or diastereomers or to their respective mixtures. The racemic forms, like the diastereomers, can be separated in a known manner into the stereoisomerically uniform constituents [cf. E. L. Eliel, Stereochemistry of Carbon Compounds, McGraw Hill, 1962].

Heterocycle in general represents a 5- to 7-membered, preferably 5- to 6-membered, saturated or unsaturated ring which as heteroatoms can contain up to 2 oxygen, sulphur and/or nitrogen atoms. Preferred 5- and 6-membered rings are those having an oxygen, sulphur and/or up to 2 nitrogen atoms. The following may be mentioned as preferred: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

A 5- to 6-membered, saturated heterocycle which, as hetero atoms, can additionally contain up to 2 oxygen, sulphur and/or nitrogen atoms, is in general azetidinyl, piperidyl, morpholinyl, piperazinyl or pyrrolidyl. Morpholinyl is preferred.

Preferred compounds of the general formula (I) are those
in which
A, D, G, L, M and T are identical or different and represent the CH group or a nitrogen atom, but where at least one of the radicals and in each case at most one of the radicals in each cycle may represent a nitrogen atom,
V represents a radical of the formula

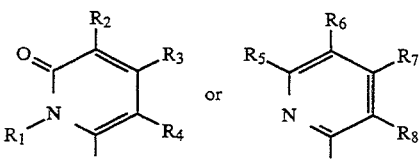

in which
R$^1$ denotes hydrogen, straight-chain or branched alkyl in each case having up to 8 carbon atoms, which is optionally substituted by cyclopropyl, cyclopentyl, cyclohexyl or hydroxyl or by straight-chain or branched alkoxy or alkylthio in each case having up to 4 carbon atoms, or denotes cyclopropyl, cyclopentyl or cyclohexyl,
R$^2$, R$^5$ and R$^6$ are identical or different and denote hydrogen, hydroxyl, nitro, cyano, formyl, fluorine, chlorine, bromine or iodine, or denote straight-chain or branched alkyl, alkenyl, alkinyl, alkoxy or alkylthio in each case having up to 6 carbon atoms, each of which is optionally substituted by hydroxyl, cyano, fluorine, chlorine, bromine, carboxyl, straight-chain or branched alkoxy, acyl or alkoxycarbonyl in each case having up to 4 carbon atoms, or by benzyl, phenyl, phenoxy, benzoyl or thienyl, where the cycles for their part can be substituted by trifluoromethoxy, trifluoromethyl, hydroxymethyl, fluorine, chlorine, bromine or iodine or by straight-chain or branched alkyl or alkoxy in each case having up to 6 carbon atoms, or denote straight-chain or branched acyl or alkoxycarbonyl in each case having up to 6 carbon atoms, phenoxycarbonyl, benzyloxycarbonyl or carboxyl, or denote tetrazolyl, which is optionally substituted by triphenylmethyl or by straight-chain or branched alkyl having up to 5 carbon atoms, which for its part can be substituted by cyano, fluorine, chlorine, bromine, carboxyl or hydroxyl or by straight-chain or branched alkoxy or alkoxycarbonyl in each case having up to 4 carbon atoms, or denote a group of the formula

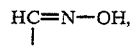

—NR$^{13}$R$^{14}$, —CO—NR$^{15}$R$^{16}$, —CH$_2$—OR$^{17}$ or —S-(O)$_a$—R$^{18}$
in which
R$^{13}$, R$^{14}$, R$^{15}$ and R$^{16}$ are identical or different and denote hydrogen, cyclopropyl, cyclopentyl or cyclohexyl or straight-chain or branched alkyl having up to 6 carbon atoms, which is optionally substituted by phenyl,
R$^{17}$ denotes straight-chain or branched acyl having up to 6 carbon atoms or benzoyl,
R$^{18}$ denotes straight-chain or branched alkyl having up to 6 carbon atoms,
a denotes a number 1 or 2,
R$^3$ and R$^7$ are identical or different and denote hydrogen, hydroxyl, carboxyl, straight-chain or branched alkoxy or alkoxycarbonyl in each case having up to 6 carbon atoms, or denote a group of the formula —NR$^{19}$R$^{20}$,
in which
R$^{19}$ and R$^{20}$ have the abovementioned meaning of R$^{13}$ and R$^{14}$ and are identical to or different from this, or denote phenyl, which can optionally be substituted by trifluoromethoxy, trifluoromethyl, hydroxymethyl, fluorine, chlorine, bromine or iodine or by straight-chain or branched alkyl or alkoxy in each case having up to 6 carbon atoms, or denote straight-chain or branched alkyl or alkenyl in each case having up to 6 carbon atoms, each of which is optionally substituted by hydroxyl, cyano, fluorine, chlorine, bromine, carboxyl or straight-chain or branched alkoxy, acyl or alkoxycarbonyl in each case having up to 4 carbon atoms, or by benzyl, phenyl, phenoxy, benzoyl or thienyl, where the cycles for their part can be substituted by trifluoromethoxy, trifluoromethyl, hydroxymethyl, fluorine, chlorine, bromine or iodine or by straight-chain or branched alkyl or alkoxy in each case having up to 6 carbon atoms,
R$^4$ denotes hydrogen, nitro, carboxyl or straight-chain or branched alkoxycarbonyl having up to 6 carbon atoms, or denotes a group of the formula —NR$^{21}$R$^{22}$,
in which
R$^{21}$ and R$^{22}$ have the abovementioned meaning of R$^{13}$ and R$^{14}$ and are identical to or different from this, or denotes straight-chain or branched alkyl or alkenyl in each case having up to 6 carbon atoms, each of which is optionally substituted by hydroxyl, cyano, fluorine, chlorine, bromine, carboxyl or straight-chain or branched alkoxy, acyl or alkoxycarbonyl in each case having up to 4 carbon atoms, or by benzyl, phenyl, phenoxy, benzoyl or thienyl, where the cycles for their part can be substituted by trifluoromethoxy, trifluoromethyl, hydroxymethyl, fluorine, chlorine, bromine or iodine or by straight-chain or branched alkyl or alkoxy in each case having up to 6 carbon atoms, $R^4$ has the abovementioned meaning of $R^1$ and $R^8$ and is identical to or different from this, W represents the

group, or represents a group of the formula

in which
X denotes hydrogen or straight-chain or branched alkyl having up to 7 carbon atoms,
$R^9$, $R^{10}$ and $R^{11}$ are identical or different and represent hydrogen, fluorine, chlorine, bromine, trifluoromethyl, hydroxyl or amido or represent straight-chain or branched alkyl, alkoxy or alkoxycarbonyl in each case having up to 4 carbon atoms,
$R^{12}$ represents a group of the formula $-CO-R^{23}$, $-SO_2R^{24}$, $-CO-NR^{25}R^{26}$, $-NH-SO_2R^{27}$ or $-SO_2NR^{28}R^{29}$,
in which
$R^{23}$ denotes hydroxyl or straight-chain or branched alkoxy having up to 4 carbon atoms,
$R^{24}$ denotes straight-chain or branched alkyl having up to 4 carbon atoms, benzyl, trifluoromethyl or p-tolyl,
$R^{25}$ and $R^{26}$ are identical or different and have the abovementioned meaning of $R^{13}$ and $R^{14}$ or
$R^{25}$ denotes hydrogen and
$R^{26}$ denotes the group $-SO_2R^{24}$,
in which
$R^{24}$ has the abovementioned meaning,
$R^{27}$ has the abovementioned meaning of $R^{24}$ and is identical to or different from this,
$R^{28}$ and $R^{29}$ have the abovementioned meaning of $R^{13}$ and $R^{14}$ and are identical to or different from this, or
$R^{28}$ denotes hydrogen or methyl,
$R^{29}$ has the abovementioned meaning of $R^{24}$ and is identical to or different from this,
$R^{12}$ represents a radical of the formula

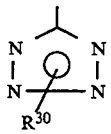

in which
$R^{30}$ denotes hydrogen or straight-chain or branched alkyl having up to 6 carbon atoms, which is optionally substituted by straight-chain or branched acyl having up to 4 carbon atoms or denotes the triphenylmethyl group, and their salts.

Particularly preferred compounds of the general formula (I) are those in which
A, D, G, L, M and T are identical or different and represent the CH group or a nitrogen atom, but where at least one of the radicals and in each case at most one of the radicals in each cycle may represent a nitrogen atom, V represents a radical of the formula

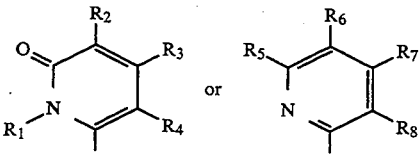

in which
$R^1$ denotes hydrogen or straight-chain or branched alkyl having up to 6 carbon atoms, which is optionally substituted by cyclopropyl, hydroxyl or straight-chain or branched alkoxy or alkylthio in each case having up to 3 carbon atoms or denotes cyclopropyl, chlorine or iodine,
$R^2$ and $R^6$ are identical or different and denote hydrogen, hydroxyl, nitro, cyano, formyl, fluorine, chlorine, bromine or iodine, or denote straight-chain or branched alkyl alkenyl, alkinyl, alkoxy or alkylthio in each case having up to 4 carbon atoms, each of which can optionally be substituted by hydroxyl or cyano or by straight-chain or branched alkoxy or alkoxycarbonyl in each case having up to 3 carbon atoms, benzyl, phenyl, phenoxy or benzoyl, denote straight-chain or branched acyl or alkoxycarbonyl in each case having up to 4 carbon atoms, phenoxycarbonyl, benzyloxycarbonyl or carboxyl, or denote tetrazolyl which is optionally substituted by triphenylmethyl or by straight-chain or branched alkyl having up to 4 carbon atoms, which for its part can be substituted by cyano, fluorine, chlorine, bromine, carboxyl or hydroxyl or by straight-chain or branched alkoxy or alkoxycarbonyl in each case having up to 3 carbon atoms, or denote a group of the formula

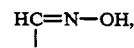

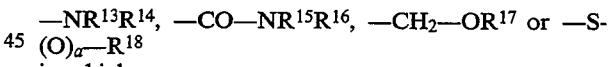

in which
$R^{13}$, $R^{14}$, $R^{15}$ and $R^{16}$ are identical or different and denote hydrogen, cyclopropyl, cyclopentyl or straight-chain or branched alkyl having up to 4 carbon atoms, which is optionally substituted by phenyl,
$R^{17}$ denotes straight-chain or branched acyl having up to 4 carbon atoms or benzoyl,
$R^{18}$ denotes straight-chain or branched alkyl having up to 4 carbon atoms,
a denotes a number 1 or 2,
$R^5$ denotes hydroxyl or straight-chain or branched alkyl having up to 6 carbon atoms,
$R^3$ and $R^7$ are identical or different and denote hydrogen, hydroxyl, carboxyl, straight-chain or branched alkoxy or alkoxycarbonyl in each case having up to 4 carbon atoms, or denote a group of the formula $-NR^{19}R^{20}$,
in which
$R^{19}$ and $R^{20}$ have the abovementioned meaning of $R^{13}$ and $R^{14}$ and are identical to or different from this, or denote phenyl which is optionally substituted by hydroxyl or cyano or by straight-chain or branched alkoxy or alkoxycarbonyl in each case having up to 3 carbon atoms, benzyl, phenyl, phenoxy or benzoyl, or denote vinyl or straight-chain or branched alkyl having up to 5 carbon atoms, which is optionally substituted by hydroxyl or cyano or by straight-chain or branched alkoxy or alkoxycarbonyl in each case having up to 3 carbon atoms, benzyl, phenyl, phenoxy or benzoyl, $R^4$ denotes hydrogen, nitro, carboxyl or straight-chain or branched alkoxycarbonyl having up to 4 carbon atoms, or denotes a group of the formula —$NR^{21}R^{22}$, in which $R^{21}$ and $R^{22}$ have the abovementioned meaning of $R^{13}$ and $R^{14}$ and are identical to or different from this, or denotes vinyl or straight-chain or branched alkyl having up to 4 carbon atoms, which is optionally substituted by hydroxyl or cyano or by straight-chain or branched alkoxy or alkoxycarbonyl in each case having up to 3 carbon atoms, benzyl, phenyl, phenoxy or benzoyl, $R^4$ has the abovementioned meaning of $R^1$ and $R^8$ and is identical to or different from this, W represents the

group, or represents a group of the formula

in which

X denotes hydrogen or straight-chain or branched alkyl having up to 5 carbon atoms, $R^9$, $R^{10}$ and $R^{11}$ are identical or different and represent hydrogen, hydroxyl, fluorine, chlorine, bromine or methyl, $R^{12}$ represents a group of the formula —$CO$—$R^{23}$, —$SO_2$—$R^{24}$, —$CO$—$NR^{25}R^{26}$, —$NH$—$SO_2R^{27}$ or —$SO_2$—$NR^{28}R^{29}$, in which $R^{23}$ denotes hydroxyl or straight-chain or branched alkoxy having up to 3 carbon atoms, $R^{24}$ denotes methyl, trifluoromethyl, benzyl or p-tolyl, $R^{25}$ and $R^{26}$ are identical or different and have the abovementioned meaning of $R^{13}$ and $R^{14}$ or $R^{25}$ denotes hydrogen and $R^{26}$ denotes the group —$SO_2$—$R^{24}$, in which $R^{24}$ has the abovementioned meaning, $R^{27}$ has the abovementioned meaning of $R^{24}$ and is identical to or different from this, $R^{28}$ and $R^{29}$ have the abovementioned meaning of $R^{13}$ and $R^{14}$ and are identical to or different from this, or $R^{28}$ denotes hydrogen or methyl and $R^{29}$ has the abovementioned meaning of $R^{24}$ and is identical to or different from this, $R^{12}$ represents the tetrazolyl radical of the formula

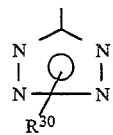

in which $R^{30}$ denotes hydrogen or straight-chain or branched alkyl having up to 4 carbon atoms, which is optionally substituted by straight-chain or branched acyl having up to 4 carbon atoms or denotes the triphenylmethyl group, and their salts.

A process for the preparation of the compounds of the general formula (I) according to the invention has additionally been found, characterized in that compounds of the general formula (II)

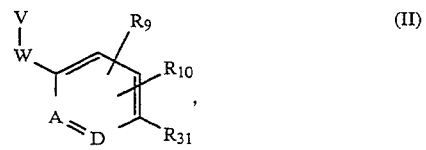

in which

A, D, V, W, $R^9$ and $R^{10}$ have the abovementioned meaning and $R^{31}$ represents a typical leaving group, such as, for example, bromine, iodine, methane-, toluene-, fluoro- or trifluoromethanesulphonyloxy, preferably bromine, are reacted with compounds of the general formula (III) or (IIIa)

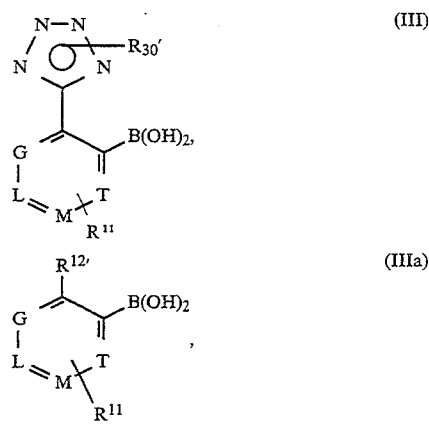

in which

G, L, M, T and $R^{11}$ have the abovementioned meaning, $R^{30'}$ represents hydrogen or the triphenylmethyl group, and $R^{12'}$ has the abovementioned meaning of $R^{12}$, but does not represent the tetrazolyl radical, in inert solvents, in the presence of a base and with metal catalysis, and then, if $R^{30'}$=a triphenylmethyl group, it is removed with acids in organic solvents and/or water according to customary conditions, and, if appropriate, in the case of the carbonyl radicals mentioned under the substituents $R^{12}$ the products are derivatized after hydrolysis of the respective esters, for example by amidation or sulphoamidation according to customary methods, and in the case of the salts preferably starting from the free tetrazole ($R^{12}/R^{30'}=H$), are reacted with acids or bases, and in the case of the free acid $R^{12}=CO_2H$ and the free tetrazole $R^{30}=H$, starting from the disalts, are reacted with acids, and, if appropriate, the substituents $R^1$, $R^2$, $R^3$, $R^4$, $R^5$, $R^6$, $R^7$, $R^8$, $R^9$, $R^{10}$, $R^{11}$ and $R^{12}$ are also varied by known methods in any process step.

The process according to the invention can be illustrated by way of example by the following reaction scheme:

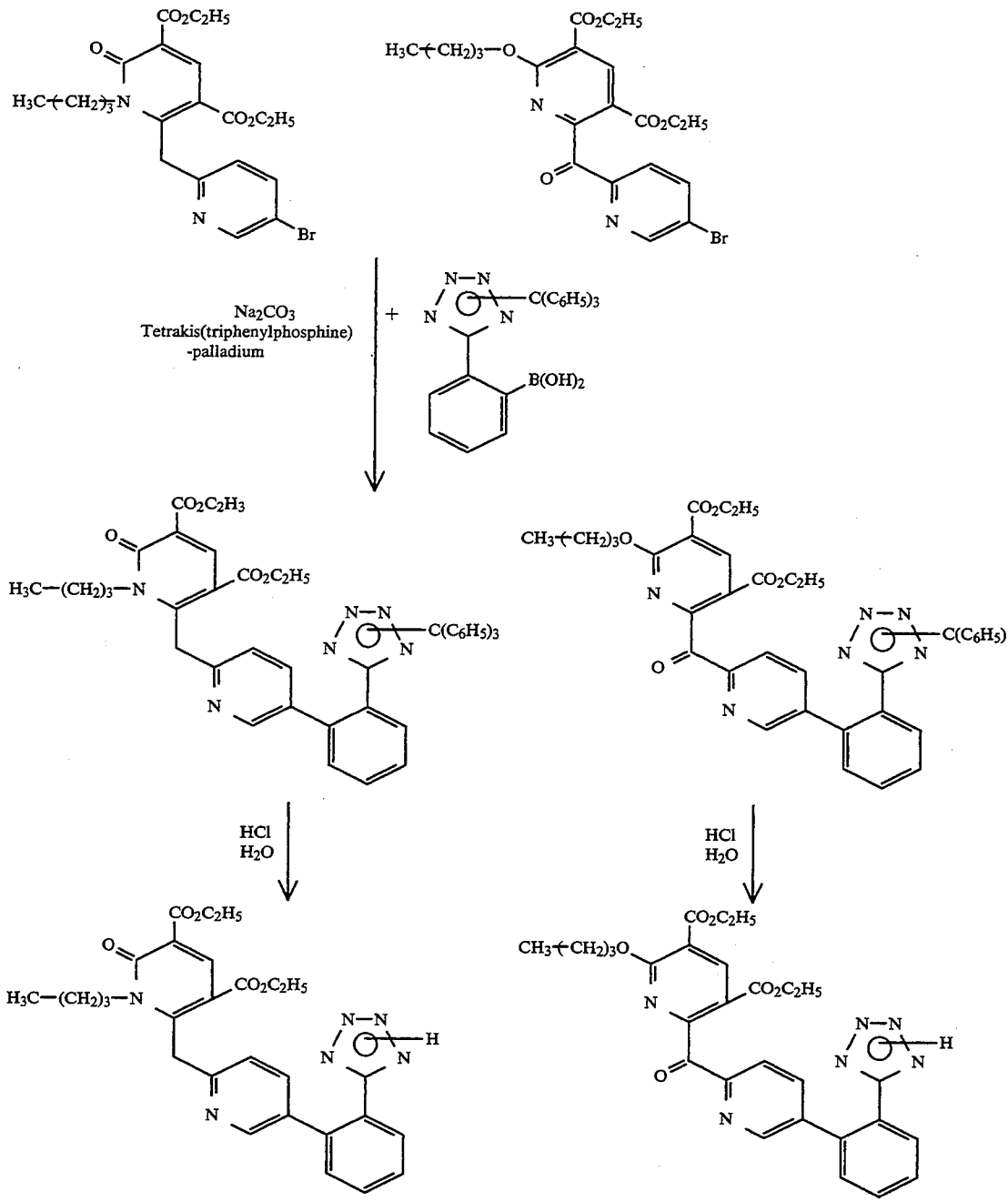

Suitable solvents for the process are the customary organic solvents which do not change under the reaction conditions. These preferably include water or alcohols, such as, for example, methanol, ethanol and propanol, ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide or dimethoxyethane, hexamethylphosphoramide, acetonitrile, acetone or nitromethane. It is also possible to use mixtures of the solvents mentioned. Tetrahydrofuran, acetone, dimethylformamide, dimethoxyethane, toluene and methanol/water are preferred.

Bases which can be employed for the process according to the invention are in general inorganic or organic bases. These preferably include alkali metalhydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate or caesium carbonate, or alkali metal or alkaline earth metal alkoxides or amides such as sodium methoxide or potassium methoxide, sodium ethoxide or potassium ethoxide or potassium tert-butoxide, thallium carbonate or hydroxide, or lithium diisopropylamide (LDA) or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals, such as sodium or their hydrides such as sodium hydride. Potassium carbonate, sodium hydride, potassium tert-butoxide, caesium carbonate, sodium carbonate, or thallium hydroxide or carbonate are preferred.

In general, the base is employed in an amount from 0.05 mol to 10 mol, preferably from 1 mol to 2 mol, in each case relative to 1 mol of the compound of the formula (III).

The process according to the invention is in general carried out in a temperature range from −100° C. to +100° C., preferably from 0° C. to 80° C., and under a protective gas atmosphere.

Suitable catalysts are in general metal complexes of nickel, palladium or platinum, preferably palladium(0) complexes such as, for example, tetrakistriphenylphosphinepalladium. It is also possible to employ phase-transfer catalysts, such as, for example, tetra-n-butylammonium bromide or crown ethers. Suitable catalysts are additionally potassium iodide or sodium iodide, preferably sodium iodide.

The process according to the invention is in general carried out at normal pressure. However, it is also possible to carry out the process at elevated pressure or at reduced pressure (for example in a range from 0.5 to 5 bar).

The triphenylmethyl group is removed with acetic acid or trifluoroacetic acid and water or one of the above-mentioned alcohols or with aqueous hydrochloric acid in the presence of acetone or likewise with alcohols.

Removal in general takes place in a temperature range from 0° C. to 150° C., preferably from 20° C. to 100° C., and at normal pressure.

Alkylation in general takes place with alkylating agents such as, for example, ($C_1$–$C_6$)-alkyl halides, sulphonic acid esters or substituted or unsubstituted ($C_1$–$C_6$) -dialkyl- or ($C_1$–$C_6$)-diaryl sulphonates, preferably methyl iodide or dimethyl sulphate.

Alkylation in general takes place in one of the abovementioned solvents, preferably in dimethylformamide, in a temperature range from 0° C. to +70° C., preferably from 0° C. to +30° C., and at normal pressure.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogencarbonate, or alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis can optionally also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out with acids, such as, for example, hydrochloric acid or trifluoroacetic acid, in the presence of one of the above-mentioned solvents and/or water or their mixtures, preferably with dioxane or tetrahydrofuran.

The amidation and the sulphonamidation are in general carried out in one of the abovementioned solvents, preferably in tetrahydrofuran or dichloromethane.

The amidation and the sulphonamidation can optionally proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from −20° C. to +80° C., preferably from −10° C. to +30° C., and at normal pressure.

Suitable bases for this in addition to the abovementioned bases are preferably triethylamine and/or dimethylaminopyridine, DBU or DABCO.

The base is employed in an amount from 0.5 mol to 10 mol, preferably from 1 mol to 2 mol, relative to 1 mol of the appropriate acid or ester.

Acid-binding agents which can be employed for the sulphonamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[4.3.0]-non-5-ene (DBN) or 1,5-diazabicyclo[5.4.0]-undec-5-ene (DBU). Potassium carbonate is preferred.

Suitable dehydrating reagents are carbodiimides such for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonateorpropanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The compounds of the general formula (II) are for the most part new and can be prepared, for example, by in the case where V represents the radical of the formula

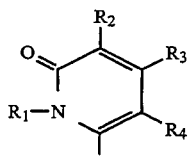

and W denotes the

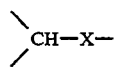

group, reacting compounds of the general formula (IV)

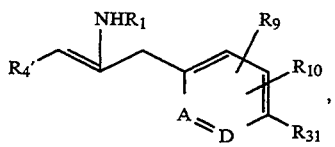 (IV)

in which
A, D, $R^1$, $R^9$, $R^{10}$ and $R^{31}$ have the abovementioned meaning and
$R^{4'}$ represents nitrile or one of the chemically useful radicals mentioned above under $R^4$, preferably ($C_1$–$C_4$)-alkoxycarbonyl, nitro or nitrile, with compounds of the general formula (V)

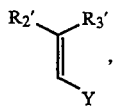 (V)

in which
$R^{2'}$ and $R^{3'}$ are identical or different and represent nitrile or one of the chemically useful radicals mentioned above under $R^2$ and $R^3$, preferably ($C_1$–$C_4$)-alkoxycarbonyl or nitrile, and
Y represents ($C_1$–$C_4$)-alkoxy or ($C_1$–$C_4$)-dialkylamino.

The reduction proceeds in a temperature range from +50° C. to +130° C., preferably from +70° C. to +110° C., and at normal pressure.

The compounds of the general formula (IV) are known in some cases or are new and can then be prepared, for example, by reacting compounds of the general formula (VI)

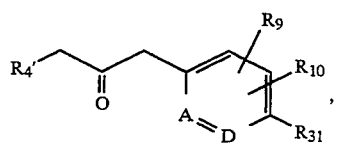 (VI)

in which
A, D, $R^{4'}$, $R^9$, $R^{10}$ and $R^{31}$ have the abovementioned meaning, in one of the above-mentioned solvents, preferably ethanol, with ammonia ($R^1$=H) or with amines of the general formula (VII)

$H_2N-R^1$ (VII), in which
$R^1$ has the abovementioned meaning.

The reaction in general proceeds in a temperature range from −10° C. to +100° C., preferably from 0° C. to +100° C.

The amines of the general formula (VII) are known.

The compounds of the general formula (VI) are known in some cases or are new and can then be prepared, for example, by reacting compounds of the general formula (VIII)

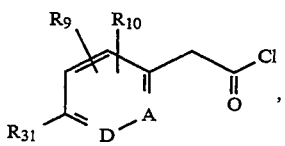 (VIII)

in which
$R^9$, $R^{10}$ and $R^{31}$ have the abovementioned meaning, with compounds of the general formula (IX)

$R^{4'}-CH_2-CO_2H$ (IX), in which
$R^{4'}$ has the abovementioned meaning, in one of the abovementioned solvents, preferably tetrahydrofuran.

The reaction is carried out in a temperature range from 0° C. to +40° C., preferably at +20° C.

The compounds of the general formulae (VIII) and (IX) are known per se.

The compounds of the general formula (II), in which V represents the radical of the formula

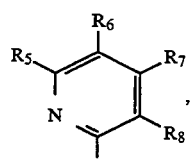

are also new and can be prepared, for example, by first reacting compounds of the general formula (IIa)

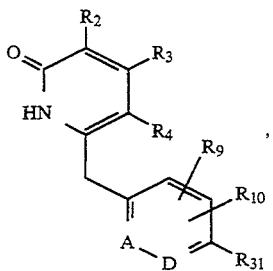

in which

A, D, R$^2$, R$^3$, R$^4$, R$^9$, R$^{10}$ and R$^{31}$ have the abovementioned meaning, in one of the above-mentioned solvents, preferably dimethylformamide, in the presence of a base, preferably caesium carbonate, with compounds of the general formula (x)

$$R^1—Z \qquad (X),$$

in which

R$^1$ has the abovementioned meaning, but preferably represents (C$_1$–C$_6$)-alkyl and Z represents halogen, preferably iodine.

In this alkylation, the compounds of the general formula (II) in which W represents the C=O group additionally result.

The reaction is in general carried out in a temperature range from 0° C. to +50° C., preferably from +10° C. to +30° C., and at normal pressure.

The base is employed in an amount from 1 mol to 10 mol, preferably from 1 mol to 3 mol, relative to 1 mol of the compounds of the general formula (X).

The compounds of the general formula (IIa) are new and can be prepared as described above.

The compounds of the general formula (X) are known.

The compounds of the general formula (III) are known in some cases or if R$^{30}$=H are new and can then be prepared by first reacting phenyltetrazole under a protective gas atmosphere, in an aprotic solvent and in the presence of a base, then adding trimethyl borate and in a last step hydrolysing with acids.

Suitable solvents for the process are aprotic solvents such as ethers, for example tetrahydrofuran, diethyl ether, toluene, hexane or benzene. Tetrahydrofuran is preferred.

Suitable bases are n-, sec- and tert-butyllithium and phenyllithium. n-Butyllithium is preferred.

The base is employed in an amount from 2 mol to 5 mol, preferably from 2 mol to 3 mol, relative to 1 mol of phenyltetrazole.

Suitable acids are in general mineral acids, such as, for example, hydrochloric acid, C$_1$–C$_4$-carboxylic acids, such as, for example, acetic acid, or phosphoric acid. Hydrochloric acid is preferred.

The acid is in general employed in an amount from 1 mol to 10 mol, preferably from 1 mol to 3 mol.

The process is in general carried out in a temperature range from −70° C. to +25° C., preferably at −10° C. to 0° C.

The process according to the invention is in general carried out at normal pressure. However, it is also possible to carry out the process at reduced pressure or at elevated pressure (for example in a range from 0.5 to 5 bar).

The compounds of the general formula (IIIa) are known in some cases or can be prepared by customary methods.

The above preparation processes are only given for clarification. The preparation of the compounds of the general formula (I) according to the invention is not restricted to these processes, and any modification of these processes is applicable to the preparation in the same manner.

The phenylpyrinylmethyl-substituted 2-oxo-1,2-dihydropyridines and pyridones according to the invention exhibit an unforeseeable, useful spectrum of pharmacological action.

The compounds according to the invention have a specific A II-antagonistic action, since they competitively inhibit the binding of angiotensin II to the receptors. They suppress the vasoconstrictor and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, disorders of cerebral function, ischaemic brain diseases, peripheral circulatory disorders, functional disorders of the kidney and adrenal gland, bronchospastic diseases of the respiratory passages having a vascular cause, sodium retention and oedemas.

The compounds can also be used for the control of glaucoma, diabetic retinopathy and increases in the mobility of the intraocular retinal fluid.

They are also suitable for controlling diseases of the central nervous system such as for example depression, migraine, schizophrenia or anxiety states, brain dysfunctions, strokes, diabetic nephropathy, cardiac dysrhythmias, or for the prophylaxis of coronary heart diseases or restenosis after angioplasty and vascular surgery.

Investigation of the Inhibition of the Contraction Induced by Agonists

Rabbits of both sexes are stunned by a blow to the neck and bled out, or in some cases anaesthetized with Nembutal (about 60–80 mg/kg i.v.) and sacrificed by opening the thorax. The thorax aorta is removed, freed of adhering connective tissue, divided into 1.5 mm wide ring segments and individually transferred under an initial loading of about 3.5 g to 10 ml organ baths containing 95% O$_2$, 5% CO$_2$-aerated Krebs-Henseleit nutrient solution temperature-controlled at 37 ° C. and of the following composition: 119 mmol/l of NaCl; 2.5 mmol/l of CaCl$_2$×2 H$_2$O; 1.2 mmol/l of KH$_2$PO$_4$; 10 mmol/l of glucose; 4.8 mmol/l of KCl; 1.4 mmol/l of MgSO$_4$×7 H$_2$O and 25 mmol/l of NaHCO$_3$.

The contractions are detected isometrically by Statham UC2 cells by means of bridge amplifiers (ifd Mülheim or DSM Aalen) and digitalized and analysed by means of an A/D converter (System 570, Keithley Munich). The agonist dose-response curves (DRC) are carried out hourly. With each DRC, 3 or 4 individual concentrations are applied to the baths at 4 min intervals. After the end of the DRC and subsequent washing-out cycles (16 times, in each case about 5 sec/min with the abovementioned nutrient solution), a 28-minute resting or incubation phase follows, in the course of which the contractions as a rule reach the starting value again.

The height of the 3rd DRC, in the normal case, is used as a reference quantity for the assessment of the test substance to be investigated in other passages, which is applied to the baths in the following DRCs in increasing dosage in each case at the start of the incubation time. Each aorta ring is in this way stimulated for the whole day, always with the same agonist.

Agonists and their standard concentrations (application volume per individual dose = 100 μl):

| | | |
|---|---|---|
| KCl | 22.7; 32.7; 42.7; 52.7 | mmol/l |
| Noradrenaline | $3 \times 10^{-9}; 3 \times 10^{-8}; 3 \times 10^{-7}; 3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamine | $10^{-7}; 10^{-6}; 10^{-5}$ | g/ml |
| Angiotensin II | $3 \times 10^{-9}; 10^{-8}; 3 \times 10^{-8}; 10^{-7}$ | g/ml |

For the calculation of the $IC_{50}$ (concentration at which the substance to be investigated causes a 50% inhibition), the effect is in each case based on the 3rd = submaximal agonist concentration.

The compounds according to the invention inhibit the contraction of the isolated rabbit aorta induced by angiotensin II in a dose-dependent manner. The contraction induced by potassium depolarization or other agonists was not inhibited or only weakly inhibited at high concentrations.

Blood pressure measurements on the angiotensin II-infused rat

Male Wistar rats (Moellegaard, Copenhagen, Denmark) having a body weight of 300–350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), angiotensin II infusion (0.3 μg/kg/min) is started. As soon as the blood pressure values have reached a stable plateau, the test substances are administered either intravenously or orally as a suspension or solution in 0.5% Tylose. The blood pressure changes under the influence of the substance are indicated in the Table as average values ±SEM.

Determination of the antihypertensive activity in conscious hypertensive rats

The oral antihypertensive activity of the compounds according to the invention was tested on conscious rats having surgically induced unilateral renal arterial stenosis. To do this, the right renal artery was constricted with a silver clip of 0.18 mm internal width. In this form of hypertension, the plasma renin activity in the first six weeks after intervention is increased. The arterial blood pressure of these animals was measured in a bloodless manner at defined time intervals after substance administration using the "tail cuff". The substances to be tested were administered intragastrically ("orally") by stomach tube in various doses suspended in a Tylose suspension. The compounds according to the invention decrease the arterial blood pressure of hypertensive rats at a clinically relevant dosage.

Additionally, the compounds according to the invention inhibit the specific binding of radioactive angiotensin II in a concentration-dependent manner.

Interaction of the compounds according to the invention with the angiotensin II receptor on membrane fractions of the adrenal gland cortex (bovine)

Bovine adrenal cortices (AGC), which have been freshly removed and carefully freed of gland medulla, are comminuted in sucrose solution (0.32M) with the aid of an Ultra-Turrax (Janke & Kunkel, Staufen i.B.) to give a coarse membrane homogenate and partially purified in two centrifugation steps to give membrane fractions. The investigations of receptor binding were carried out on partially purified membrane fractions of bovine AGC using radioactive angiotensin II in an assay volume of 0.25 ml, which in detail contains the partially purified membranes (50–80 μg), $^3$H-angiotensin II (3–5 nM), test buffer solution (50 mM tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ and $IC_{50}$ values ($K_i$: $IC_{50}$ values corrected for the radioactivity used; $IC_{50}$ values: concentration at which the substance to be investigated causes a 50% inhibition of the specific binding of the radioligand).

Investigation of inhibition of the proliferation of smooth muscle cells by the compounds according to the invention To determine the antiproliferative action of the compounds, smooth muscle cells are used which have been obtained from the aorta of rats by the media explant technique [R. Ross, J. Cell. Biol. 50, 172, 1971]. The cells are inoculated into suitable culture dishes, as a rule 96-hole plates, and cultured in 5% $CO_2$ at 37° C. for 2–3 days in medium 199 containing 7.5% FCS and 7.5% NCS, 2 mM L-glutamine and 15 mM HEPES, pH 7.4. The cells are then synchronized by serum withdrawal for 2–3 days and then-stimulated into growth with serum or other factors. Test compounds are simultaneously added. After 16–20 hours, 1 μCi of $^3$H-thymidine is added and after a further 4 hours the incorporation of this substance into the TCA-precipitatable DNA of the cells is determined. To determine the $IC_{50}$ values, the active compound concentration is calculated which, on sequential dilution of the active compound, causes semi-maximal inhibition of the thymidine incorporation produced by 10% FCS.

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active substance using suitable liquid excipient materials can be employed.

In general, it has proved advantageous on intravenous administration to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

In spite of this, it may sometimes be necessary to depart from the amounts mentioned, in particular depending on the body weight or on the type of administration route, on individual behaviour towards the medicament, the manner of its formulation and the time or interval at which administration takes place. Thus, in some cases it may be sufficient to manage with less than the above-mentioned minimum amount, while in other cases the upper limit mentioned must be exceeded. In the case of the administration of relatively large amounts, it may be advisable to divide these into several individual doses over the course of the day.

We claim:

1. A pyridinylmethyl-substituted pyridine or pyridone compound of the formula

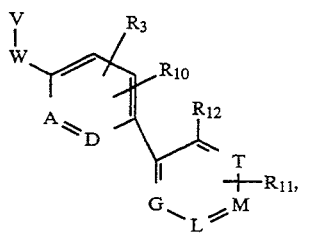

in which

A, D, G, L, M and T are identical or different and represent the CH group or a nitrogen atom, but where at least one of the radicals and in each case at most one of the radicals in each cycle may represent a nitrogen atom, V represents a radical of the formula

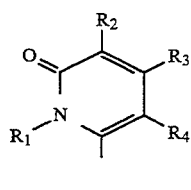

or

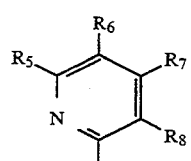

in which $R^1$ denotes straight-chain or branched alkyl having up to 10 carbon atoms, which is optionally substituted by cycloalkyl having 3 to 6 carbon atoms or hydroxyl or by straight-chain or branched alkoxy or alkylthio in each case having up to 6 carbon atoms, or denotes cycloalkyl having 3 to 6 carbon atoms, $R^2$, $R^5$ and $R^6$ are identical or different and denote hydrogen, hydroxyl, nitro, cyano, formyl or halogen, or denote straight-chain or branched alkyl, alkenyl, alkinyl, alkoxy or alkylthio in each case having up to 8 carbon atoms, each of which is optionally substituted up to 3 times by identical or different substituents which are hydroxyl, cyano, halogen, carboxyl and straight-chain or branched alkoxy, acyl or alkoxycarbonyl in each case having up to 6 carbon atoms, or by cycloalkyl having 3 to 6 carbon atoms, benzyl, phenyl, phenoxy or benzoyl or by a 5- to 7-membered, saturated or unsaturated heterocycle having up to 3 hetero atoms selected from the group consisting of S, N and O, where all cycles for their part are optionally substituted up to 2 times by identical or different substituents wherein said substituents are trifluoromethyl, trifluoromethoxy, halogen, nitro, cyano, hydroxyl or hydroxymethyl or straight-chain or branched alkyl or alkoxy in each case having up to 6 carbon atoms, or denote straight-chain or branched acyl or alkoxycarbonyl in each case having up to 8 carbon atoms, phenoxycarbonyl, benzyloxycarbonyl or carboxyl, or denote tetrazolyl, which is optionally substituted by triphenylmethyl or by straight-chain or branched alkyl having up to 6 carbon atoms, which for its part is optionally substituted by cyano, halogen, carboxyl, phenoxycarbonyl or hydroxyl or by straight-chain or branched alkoxy or alkoxycarbonyl in each case having up to 6 carbon atoms, or denote a group of the formula

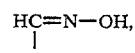

—NR$^{13}$R$^{14}$, —CO—NR$^{15}$R$^{16}$, —CH$_2$—OR$^{17}$ or S(O)$_a$—R$^{18}$ in which $R^{13}$, $R^{14}$, $R^{15}$ and $R^{16}$ are identical or different and denote hydrogen, cycloalkyl having 3 to 8 carbon atoms or straight-chain or branched alkyl having up to 8 carbon atoms, which is optionally substituted by phenyl, $R^{17}$ denotes straight-chain or branched acyl having up to 6 carbon atoms or benzoyl, $R^{18}$ denotes straight-chain or branched alkyl having up to 8 carbon atoms, a denotes a number 1 or 2, $R^3$ and $R^7$ are identical or different and denote hydrogen, hydroxyl, carboxyl, straight-chain or branched alkoxy or alkoxycarbonyl in each case having up to 8 carbon atoms, or denote a group of the formula —NR$^{19}$R$^{20}$, in which $R^{19}$ and $R^{20}$ have the abovementioned meaning of $R^{13}$ and $R^{14}$ and are identical to or different from this, or denote aryl having 6 to 10 carbon atoms, which can optionally be substituted up to 2 times by identical or different substituents wherein substituents are trifluoromethyl, trifluoromethoxy, halogen, nitro, cyano, hydroxyl and hydroxymethyl or by straight-chain or branched alkyl or alkoxy in each case having up to 6 carbon atoms, or denote straight-chain or branched alkyl or alkenyl in each case having up to 8 carbon atoms, each of which is optionally substituted up to 3 times by identical or different substituents wherein the substituents are hydroxyl, cyano, halogen, carboxyl and straight-chain or branched alkoxy, acyl or alkoxycarbonyl in each case having up to 6 carbon atoms, or by cycloalkyl having 3 to 6 carbon atoms, benzyl, phenyl, phenoxy, benzoyl or by a 5- to 7-membered, saturated or unsaturated heterocycle having up to 3 hetero atoms selected from the group consisting of S, N and O, where the cycles for their part are optionally substituted up to 2 times by identical or different substituents wherein the substituents are trifluoromethyl, trifluoromethoxy, halogen, nitro, cyano, hydroxyl or hydroxymethyl or straight-chain or branched alkyl or alkoxy in each case having up to 6 carbon atoms, $R^4$ denotes hydrogen, nitro, carboxyl or straight-chain or branched alkoxycarbonyl having up to 8 carbon atoms, or denotes a group of the formula —$NR^{21}R^{22}$, in which $R^{21}$ and $R^{22}$ have the abovementioned meaning of $R^{13}$ and $R^{14}$ and are identical to or different from this, or denotes straight-chain or branched alkyl or alkenyl in each case having up to 8 carbon atoms, each of which is optionally substituted up to 3 times by identical or different substituents wherein the substituents are hydroxyl, cyano, halogen, carboxyl and straight-chain or branched alkoxy, acyl or alkoxycarbonyl in each case having up to 6 carbon atoms or by cycloalkyl having 3 to 6 carbon atoms, benzyl, phenyl, phenoxy or benzoyl or by a 5- to 7-membered saturated or unsaturated heterocycle having up to 3 hetero atoms selected from the group consisting of S, N and O, where all cycles for their part can be substituted up to 2 times by identical or different substituents wherein the substituents are trifluoromethyl, trifluoromethoxy hydroxymethyl or straight-chain or branched alkyl or alkoxy in each case having up to 6 carbon atoms, $R^8$ has the abovementioned meaning of $R^1$ and $R^4$ and is identical to or different from this, W represents the

group, or represents a group of the formula

in which

X denotes hydrogen or straight-chain or branched alkyl having up to 8 carbon atoms, $R^9$, $R^{10}$ and $R^{11}$ are identical or different and represent hydrogen, halogen, cyano, nitro, trifluoromethyl, hydroxyl, amido or straight-chain or branched alkyl, alkoxy or alkoxycarbonyl having up to 6 carbon atoms, represents a group of the formula —CO—$R^{23}$, —$SO_2R^{24}$, —CO—$NR^{25}R^{26}$, —NH—$SO_2R^{27}$ or —$SO_2NR^{28}R^{29}$, in which $R^{23}$ denotes hydroxyl or straight-chain or branched alkoxy having up to 6 carbon atoms, $R^{24}$ denotes hydroxyl, trifluoromethyl, straight-chain or branched alkoxy or alkyl in each case having up to 6 carbon atoms, phenyl or benzyl, each of which is optionally substituted up to 2 times by identical or different substituents selected from the group consisting of halogen, trifluoromethyl and straight-chain or branched alkyl having up to 4 carbon atoms, $R^{25}$ and $R^{26}$ are identical or different and have the abovementioned meaning of $R^{13}$ and $R^{14}$, or $R^{25}$ denotes hydrogen and $R^{26}$ denotes the group —$SO_2R^{24}$, in which $R^{24}$ has the abovementioned meaning, $R^{27}$ has the abovementioned meaning of $R^{24}$ and is identical to or different from this, $R^{28}$ and $R^{29}$ have the abovementioned meaning of $R^{13}$ and $R^{14}$ and are identical to or different from this, or $R^{28}$ denotes hydrogen or straight-chain or branched alkyl having up to 4 carbon atoms and $R^{29}$ has the abovementioned meaning of $R^{24}$ and is identical to or different from this, $R^{12}$ represents a radical of the formula

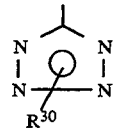

in which $R^{30}$ denotes hydrogen or straight-chain or branched alkyl having up to 8 carbon atoms, which is optionally substituted by straight-chain or branched acyl having up to 6 carbon atoms or denotes the triphenylmethyl group, or its salt.

2. A pyridinylmethyl-substituted pyridine or pyridone compound according to claim 1, in which.

A, D, G, L, M and T are identical or different and represent the CH group or a nitrogen atom, but where at least one of the radicals and in each case at most one of the radicals in each cycle may represent a nitrogen atom, V represents a radical of the formula

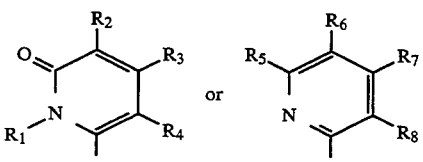

in which $R^1$ denotes hydrogen, straight-chain or branched alkyl in each case having up to 8 carbon atoms, which is optionally substituted by cyclopropyl, cyclopentyl, cyclohexyl or hydroxyl or by straight-chain or branched alkoxy or alkylthio in each case having up to 4 carbon atoms, or denotes cyclopropyl, cyclopentyl or cyclohexyl, $R^2$, $R^5$ and $R^6$ are identical or different and denote hydrogen, hydroxyl, nitro, cyano, formyl, fluorine, chlorine, bromine or iodine, or denote straight-chain or branched alkyl, alkenyl, alkinyl, alkoxy or alkylthio in each case having up to 6 carbon atoms, each of which is optionally substituted by hydroxyl, cyano, fluorine, chlorine, bromine, carboxyl, straight-chain or branched alkoxy, acyl or alkoxycarbonyl in each case having up to 4 carbon atoms, or by benzyl, phenyl, phenoxy, benzoyl or thienyl, where all cycles for their part are optionally substituted by trifluoromethoxy, trifluoromethyl, hydroxymethyl, fluorine, chlorine, bromine or iodine or straight-chain or branched alkyl or alkoxy in each case having up to 6 carbon atoms, or denote straight-chain or branched acyl or alkoxycarbonyl in each case having up to 6 carbon atoms, phenoxycarbonyl, benzyloxycarbonyl or carboxyl, or denote tetrazolyl, which is optionally substituted by triphenylmethyl or by straight-chain or branched alkyl having up to 5 carbon atoms, which for its part can be substituted by cyano, fluorine, chlorine, bromine, carboxyl or hydroxyl or by straight-chain or branched alkoxy or alkoxycarbonyl in each case having up to 4 carbon atoms, or denote a group of the formula

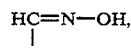

$-NR^{13}R^{14}$, $-CO-NR^{15}R^{16}$, $-CH_2-OR^{17}$ or $-S(O)_a-R^{18}$ in which $R^{13}$, $R^{14}$, $R^{15}$ and $R^{16}$ are identical or different and denote hydrogen, cyclopropyl, cyclopentyl or cyclohexyl or straight-chain or branched alkyl having up to 6 carbon atoms, which is optionally substituted by phenyl, $R^{17}$ denotes straight-chain or branched acyl having up to 6 carbon atoms or benzoyl, $R^{18}$ denotes straight-chain or branched alkyl having up to 6 carbon atoms, a denotes a number 1 or 2, $R^3$ and $R^7$ are identical or different and denote hydrogen, hydroxyl, carboxyl, straight-chain or branched alkoxy or alkoxycarbonyl in each case having up to 6 carbon atoms, or denote a group of the formula $-NR^{19}R^{20}$, in which $R^{19}$ and $R^{\circ}$ have the abovementioned meaning of $R^{13}$ and $R^{14}$ and are identical to or different from this, or denote phenyl, which is optionally be substituted by trifluoromethoxy, trifluoromethyl, hydroxymethyl, fluorine, chlorine, bromine or iodine or by straight-chain or branched alkyl or alkoxy in each case having up to 6 carbon atoms, or denote straight-chain or branched alkyl or alkenyl in each case having up to 6 carbon atoms, each of which is optionally substituted by hydroxyl, cyano, fluorine, chlorine, bromine, carboxyl or straight-chain or branched alkoxy, acyl or alkoxycarbonyl in each case having up to 4 carbon atoms, or by benzyl, phenyl, phenoxy, benzoyl or thienyl, where all cycles for their part are optionally substituted by trifluoromethoxy, trifluoromethyl, hydroxymethyl, fluorine, chlorine, bromine or iodine or straight-chain or branched alkyl or alkoxy in each case having up to 6 carbon atoms, $R^4$ denotes hydrogen, nitro, carboxyl or straight-chain or branched alkoxycarbonyl having up to 6 carbon atoms, or denotes a group of the formula $-NR^{21}R^{22}$, in which $R^{21}$ and $R^{22}$ have the abovementioned meaning of $R^{13}$ and $R^{14}$ and are identical to or different from this, or denotes straight-chain or branched alkyl or alkenyl in each case having up to 6 carbon atoms, each of which is optionally substituted by hydroxyl, cyano, fluorine, chlorine, bromine, carboxyl or straight-chain chain or branched alkoxy, acyl or alkoxycarbonyl in each case having up to 4 carbon atoms, or by benzol, phenyl, phenoxy, benzoyl or thienyl, wherein said cycles are optionally substituted by trifluoromethoxy, trifluoromethyl, hydroxymethyl, fluorine, chlorine, bromine or iodine or straight-chain or branched alkyl or alkoxy in each case having up to 6 carbon atoms, $R^4$ has the abovementioned meaning of $R^1$ and $R^8$ and is identical to or different from this, W represents the

group, or represents a group of the formula

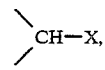

in which

X denotes hydrogen or straight-chain or branched alkyl having up to 7 carbon atoms, $R^9$, $R^{10}$ and $R^{11}$ are identical or different and represent hydrogen, fluorine, chlorine bromine, trifluoromethyl, hydroxyl or amido or represent straight-chain or branched alkyl alkoxy or alkoxycarbonyl in each case having up to 4 carbon atoms, $R^{12}$ represents a group of the formula $-CO-R^{23}$, $-SO_2R^{24}$, $-CO-NR^{25}R^{26}$, $-NH-SO_2R^{27}$ or $-SO_2NR^{28}R^{29}$, in which $R^{23}$ denotes hydroxyl or straight-chain or branched alkoxy having up to 4 carbon atoms, $R^{24}$ denotes straight-chain or branched alkyl having up to 4 carbon atoms, benzyl, trifluoromethyl or p-tolyl, $R^{25}$ and $R^{26}$ are identical or different and have the above-mentioned meaning of $R^{13}$ and $R^{14}$ or $R^{25}$ denotes hydrogen and $R^{26}$ denotes the group $-SO_2R^{24}$, in which $R^{24}$ has the abovementioned meaning, $R^{27}$ has the abovementioned meaning of $R^{24}$ and is identical to or different from this, $R^{28}$ and $R^{29}$ have the abovementioned meaning of $R^{13}$ and $R^{14}$ and are identical to or different from this, or $R^{28}$ denotes hydrogen or methyl, $R^{29}$ has the abovementioned meaning of $R^{24}$ and is identical to or different from this, $R^{12}$ represents a radical of the formula

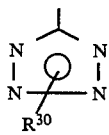

in which $R^{30}$ denotes hydrogen or straight-chain or branched alkyl having up to 6 carbon atoms, which is optionally substituted by straight-chain or branched acyl having up to 4 carbon atoms or denotes the triphenylmethyl group, or its salt. and salts.

3. A pyridinyl-methyl-substituted pyridine and pyridone compound according to claim 1, in which A, D, G, L, M and T are identical or different and represent the CH group or a nitrogen atom, but where at least one of the radicals and in each case at most one of the radicals in each cycle may represent a nitrogen atom, V represents a radical of the formula

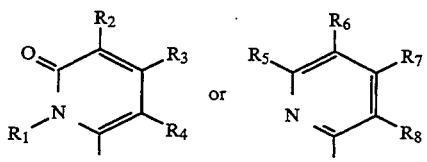

in which $R^1$ denotes hydrogen or straight-chain or branched alkyl having up to 6 carbon atoms, which is optionally substituted by cyclopropyl, hydroxyl or straight-chain or branched alkoxy or alkylthio in each case having up to 3 carbon atoms or denotes cyclopropyl, chlorine or iodine, $R^2$ and $R^6$ are identical or different and denote hydrogen, hydroxyl, nitro, cyano, formyl, fluorine, chlorine, bromine or iodine, or denote straight-chain or branched alkyl, alkenyl, alkinyl, alkoxy or alkylthio in each case having up to 4 carbon atoms, each of which is optionally be substituted by hydroxyl or cyano or by straight-chain or branched alkoxy or alkoxycarbonyl in each case having up to 3 carbon atoms, benzyl, phenyl, phenoxy or benzoyl, denote straight-chain or branched acyl or alkoxycarbonyl in each case having up to 4 carbon atoms, phenoxycarbonyl, benzyloxycarbonyl or carboxyl, or denote tetrazolyl which is optionally substituted by triphenylmethyl or by straight-chain or branched alkyl having up to 4 carbon atoms, which for its part is optionally substituted by cyano, fluorine, chlorine, bromine, carboxyl or hydroxyl or by straight-chain or branched alkoxy or alkoxycarbonyl in each case having up to 3 carbon atoms, or denote a group of the formula

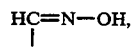

$-NR^{13}R^{14}$, $-CO-NR^{15}R^{16}$, $-CH_2-OR^{17}$ or $-S-(O)_a-R^{18}$ in which $R^{13}$, $R^{14}$, $R^{15}$ and $R^{16}$ are identical or different and denote hydrogen, cyclopropyl, cyclopentyl or straight-chain or branched alkyl having up to 4 carbon atoms, which is optionally substituted by phenyl, $R^{17}$ denotes straight-chain or branched acyl having up to 4 carbon atoms or benzoyl, $R^{18}$ denotes straight-chain or branched alkyl having up to 4 carbon atoms, a denotes a number 1 or 2, $R^5$ denotes hydroxyl or straight-chain or branched alkyl having up to 6 carbon atoms, $R^3$ and $R^7$ are identical or different and denote hydrogen, hydroxyl, carboxyl, straight-chain or branched alkoxy or alkoxycarbonyl in each case having up to 4 carbon atoms, or denote a group of the formula $-NR^{19}R^{20}$, in which $R^{19}$ and $R^{20}$ have the abovementioned meaning of $R^{13}$ and $R^{14}$ and are identical to or different from this, or denote phenyl which is optionally substituted by hydroxyl or cyano or by straight-chain or branched alkoxy or alkoxycarbonyl in each case having up to 3 carbon atoms, benzyl, phenyl, phenoxy or benzoyl, or denote vinyl or straight-chain or branched alkyl having up to 5 carbon atoms, which is optionally substituted by hydroxyl or cyano or by straight-chain or branched alkoxy or alkoxycarbonyl in each case having up to 3 carbon atoms, benzyl, phenyl, phenoxy or benzoyl, $R^4$ denotes hydrogen, nitro, carboxyl or straight-chain or branched alkoxycarbonyl having up to 4 carbon atoms, or denotes a group of the formula $-NR^{21}R^{22}$, in which $R^{21}$ and $R^{22}$ have the abovementioned meaning of $R^{13}$ and $R^{14}$ and are identical to or different from this, or denotes vinyl or straight-chain or branched alkyl having up to 4 carbon atoms, which is optionally substituted by hydroxyl or cyano or by straight-chain or branched alkoxy or alkoxycarbonyl in each case having up to 3 carbon atoms, benzyl, phenyl, phenoxy or benzoyl, $R^4$ has the abovementioned meaning of $R^1$ and $R^8$ and is identical to or different from this, W represents the

group, or represents a group of the formula

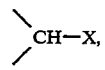

in which

X denotes hydrogen or straight-chain or branched alkyl having up to 5 carbon atoms, $R^9$, $R^{10}$ and $R^{11}$ are identical or different and represent hydrogen, hydroxyl, fluorine, chlorine, bromine or methyl, $R^{12}$ represents a group of the formula $-CO-R^{23}$, $-SO_2-R^{24}$, $-CO-NR^{25}R^{26}$, $-NH-SO_2R^{27}$ or $-SO_2-NR^{28}R^{29}$, in which $R^{23}$ denotes hydroxyl or straight-chain or branched alkoxy having up to 3 carbon atoms, $R^{24}$ denotes methyl, trifluoromethyl, benzyl or p-tolyl, $R^{25}$ and $R^{26}$ are identical or different and have the abovementioned meaning of $R^{13}$ and $R^{14}$ or $R^{25}$ denotes hydrogen and $R^{26}$ denotes the group $-SO_2-R^{24}$, in which $R^{24}$ has the abovementioned meaning, $R^{27}$ has the abovementioned meaning of $R^{24}$ and is identical to or different from this, $R^{28}$ and $R^{29}$ have the abovementioned meaning of $R^{13}$ and $R^{14}$ and are identical to or different from this, or $R^{28}$ denotes hydrogen or methyl and $R^{29}$ has the abovementioned meaning of $R^{24}$ and is identical to or different from this, $R^{12}$ represents the tetrazolyl radical of the formula

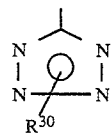

in which $R^{30}$ denotes hydrogen or straight-chain or branched alkyl having up to 4 carbon atoms, which is optionally substituted by straight-chain or branched acyl having up to 4 carbon atoms or denotes the triphenylmethyl group, or its salt.

4. A composition for the treatment of arterial hypertension and atherosclerosis comprising an amount effective therefore of a compound or salt thereof according to claim 1 and a pharmacologically acceptable diluent.

5. The method of treating arterial hypertension and atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,414,003
DATED : May 9, 1995
INVENTOR(S) : Fey, et al.

It is certified that error appears in the above-indentified patent and that said Letters Patent is hereby corrected as shown below:

Col. 1, line 38    Delete " 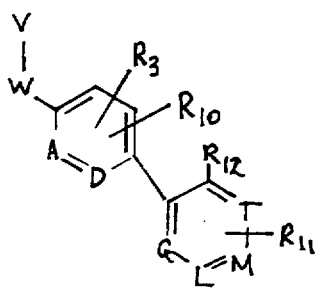 " and substitute -- 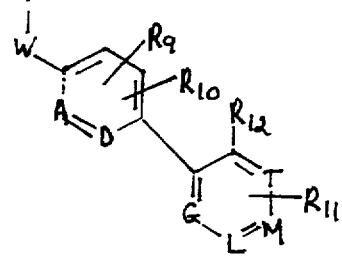 --

UNITED STATES PATENT AND TRADEMARK OFFICE
CERTIFICATE OF CORRECTION

PATENT NO. : 5,414,003
DATED : May 9, 1995
INVENTOR(S) : Fey, et al.

It is certified that error appears in the above-indentified patent and that said Letters Patent is hereby corrected as shown below:

Col. 21, line 33   Delete " 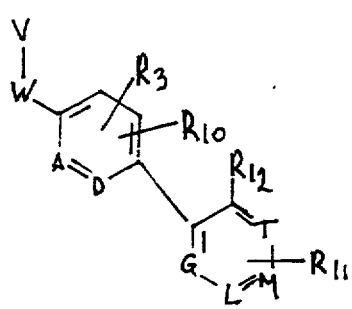   and substitute -- 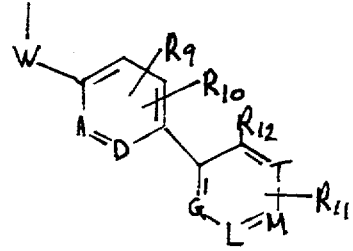   --

Col. 24, line 1    Before " represents " insert -- $R^{12}$ --

Col. 25, line 52   Delete " $R^o$ " and substitute -- $R^{20}$ --

UNITED STATES PATENT AND TRADEMARK OFFICE
CERTIFICATE OF CORRECTION

PATENT NO. : 5,414,003
DATED : May 9, 1995
INVENTOR(S) : Fey, et al.

It is certified that error appears in the above-indentified patent and that said Letters Patent is hereby corrected as shown below:

Col. 27, line 17    Delete " and salts "

Col. 28, line 20    Delete " $R^o$ " and substitute -- $R^{20}$ --

Signed and Sealed this

Fifth Day of September, 1995

Attest:

BRUCE LEHMAN

*Attesting Officer*         *Commissioner of Patents and Trademarks*